United States Patent
AlSahan et al.

(10) Patent No.: US 9,086,354 B2
(45) Date of Patent: Jul. 21, 2015

(54) SOUND-VELOCITY DEWATERING SYSTEM

(75) Inventors: Fawaz A. AlSahan, Riyadh (SA); Omar Z. AlZayed, Riyadh (SA)

(73) Assignee: SAUDI ARABIAN OIL COMPANY (SA)

( * ) Notice: Subject to any disclaimer, the term of this patent is extended or adjusted under 35 U.S.C. 154(b) by 83 days.

(21) Appl. No.: 12/841,690

(22) Filed: Jul. 22, 2010

(65) Prior Publication Data

US 2012/0017998 A1    Jan. 26, 2012

(51) Int. Cl.
*F16K 31/12* (2006.01)
*G01N 29/024* (2006.01)
*B01D 17/02* (2006.01)
*C10G 33/06* (2006.01)
*C10G 33/08* (2006.01)
(Continued)

(52) U.S. Cl.
CPC .......... *G01N 29/024* (2013.01); *B01D 17/0214* (2013.01); *C10G 33/06* (2013.01); *C10G 33/08* (2013.01); *G01N 29/4427* (2013.01); *C10G 2300/201* (2013.01); *E21B 43/34* (2013.01); *G01N 2291/02836* (2013.01); *G01N 2291/048* (2013.01); *G01N 2291/102* (2013.01)

(58) Field of Classification Search
CPC . G05D 7/0617; G05D 7/0623; G05D 7/0629; F16K 37/005; F16K 37/0091; C10G 33/02; C10G 33/08; G01N 29/024; G01N 29/4427; G01N 2291/102; B01D 17/0214; E21B 43/34
USPC ................. 137/487.5, 172; 73/61.64, 861.04, 73/861.27
See application file for complete search history.

(56) References Cited

U.S. PATENT DOCUMENTS 3,359,787 A    12/1967 Zemanek, Jr.
3,710,615 A *   1/1973 Johnson et al. ............. 73/61.75
3,849,285 A * 11/1974 Prestridge .................... 204/663
(Continued)

FOREIGN PATENT DOCUMENTS

EP    1 020 713 A1    7/2000
EP    1 593 418 A1   11/2005

OTHER PUBLICATIONS

PCT International Search Report Dated Oct. 6, 2011; International Application No. PCT/US2011/043796; International Filing Date Jul. 13, 2011; Applicant: Saudi Arabian Oil Company.
(Continued)

*Primary Examiner* — Matthew W Jellett
(74) *Attorney, Agent, or Firm* — Bracewell & Giuliani LLP; Constance Gall Rhebergen; Brad Y. Chin

(57) ABSTRACT

A method and apparatus for an improved dewatering tank system that allows for safely controlling a water stream exiting the dewatering tank system. The apparatus can include a sound velocity detector, a control system, and a control element. The sound velocity detector can include a transducer, a detector, and a transmitter. The control system can include a computer and a program product. The apparatus can optionally include a dewatering tank, a drain line, and a controllable valve. The apparatus allows for transmitting sound energy through the water stream flowing in the drain lined that is connected to the dewatering tank, calculating the velocity of the sound energy as the sound energy travels through the water stream, monitoring the velocity of the sound energy for a period of time, and controlling the position of the controllable valve depending on the calculated velocity of the sound energy.

18 Claims, 8 Drawing Sheets

(51) Int. Cl.
*G01N 29/44* (2006.01)
*E21B 43/34* (2006.01)

(56) References Cited

U.S. PATENT DOCUMENTS

| | | | | |
|---|---|---|---|---|
| 3,892,127 A | * | 7/1975 | Cirulis et al. | 73/61.49 |
| 3,973,430 A | * | 8/1976 | Cirulis et al. | 73/61.49 |
| 4,080,837 A | * | 3/1978 | Alexander et al. | 73/61.45 |
| 4,236,406 A | | 12/1980 | Reed et al. | |
| 4,573,346 A | | 3/1986 | Zacharias, Jr. | |
| 4,596,133 A | * | 6/1986 | Smalling et al. | 73/24.01 |
| 4,596,136 A | | 6/1986 | Zacharias, Jr. | |
| 4,656,869 A | * | 4/1987 | Zacharias | 73/597 |
| 5,090,238 A | * | 2/1992 | Jones | 73/152.42 |
| 5,139,653 A | * | 8/1992 | Ludlam et al. | 210/85 |
| 5,473,934 A | * | 12/1995 | Cobb | 73/61.49 |
| 5,616,856 A | | 4/1997 | Castel | |
| 5,935,427 A | * | 8/1999 | Witter et al. | 210/93 |
| 5,953,287 A | | 9/1999 | Willacy et al. | |
| 7,228,740 B2 | * | 6/2007 | Sinha | 73/579 |
| 2004/0173021 A1 | | 9/2004 | Lizon et al. | |
| 2005/0210965 A1 | | 9/2005 | Sinha | |
| 2006/0037385 A1 | | 2/2006 | Gysling | |
| 2006/0174707 A1 | | 8/2006 | Zhang | |
| 2006/0211128 A1 | | 9/2006 | Johnson et al. | |
| 2007/0204689 A1 | | 9/2007 | Bostrom | |
| 2008/0124595 A1 | | 5/2008 | Muramatsu | |
| 2008/0208483 A1 | | 8/2008 | Loose et al. | |
| 2009/0025460 A1 | | 1/2009 | Hurmuzlu et al. | |
| 2009/0126481 A1 | | 5/2009 | Burris | |
| 2013/0082010 A1 | * | 4/2013 | Al-Mulhim et al. | 210/767 |

OTHER PUBLICATIONS

Written Opinion issued in International Application No. PCT/US2011/043796, dated Aug. 20, 2012 (8 pages).

* cited by examiner

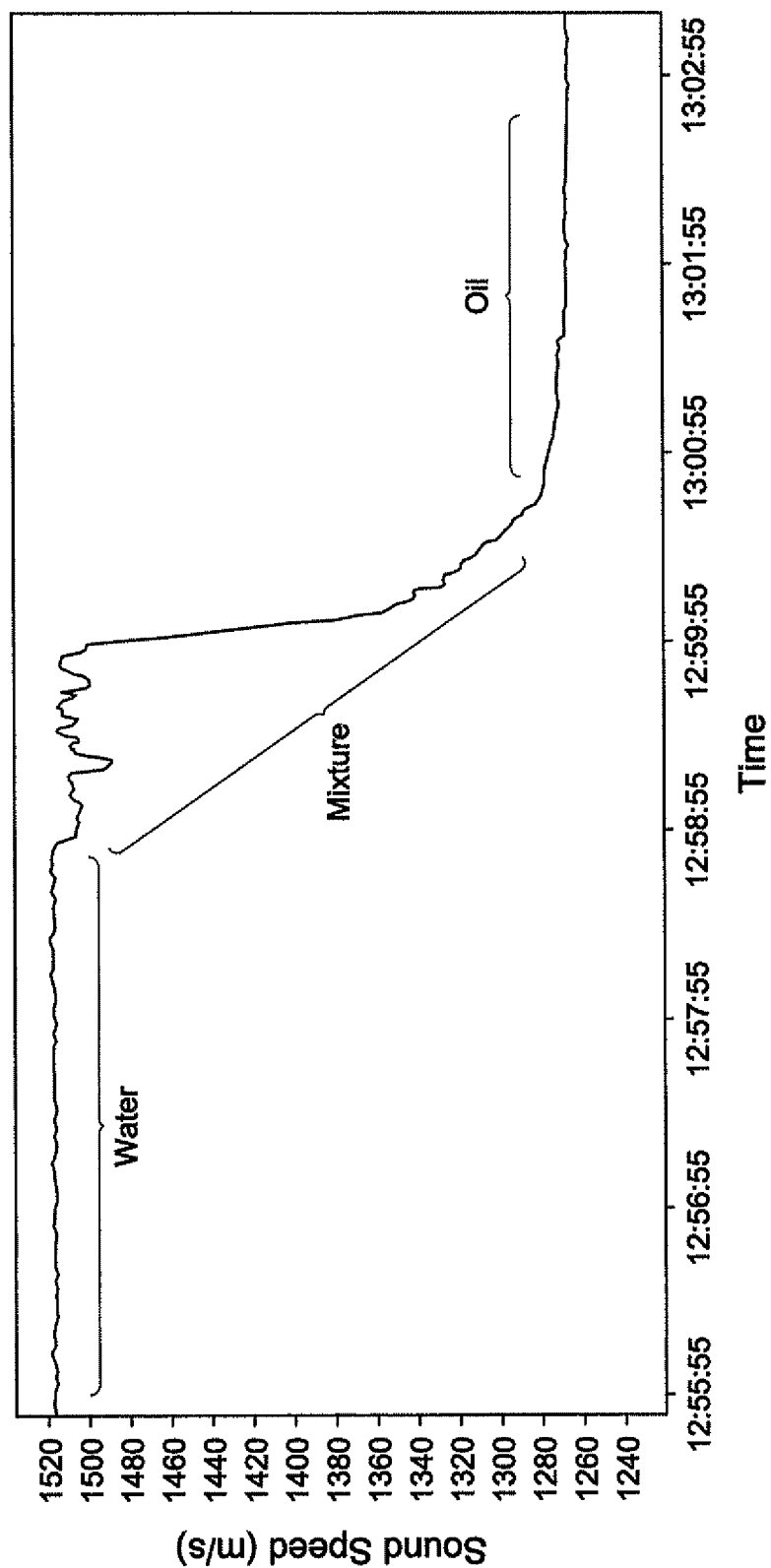

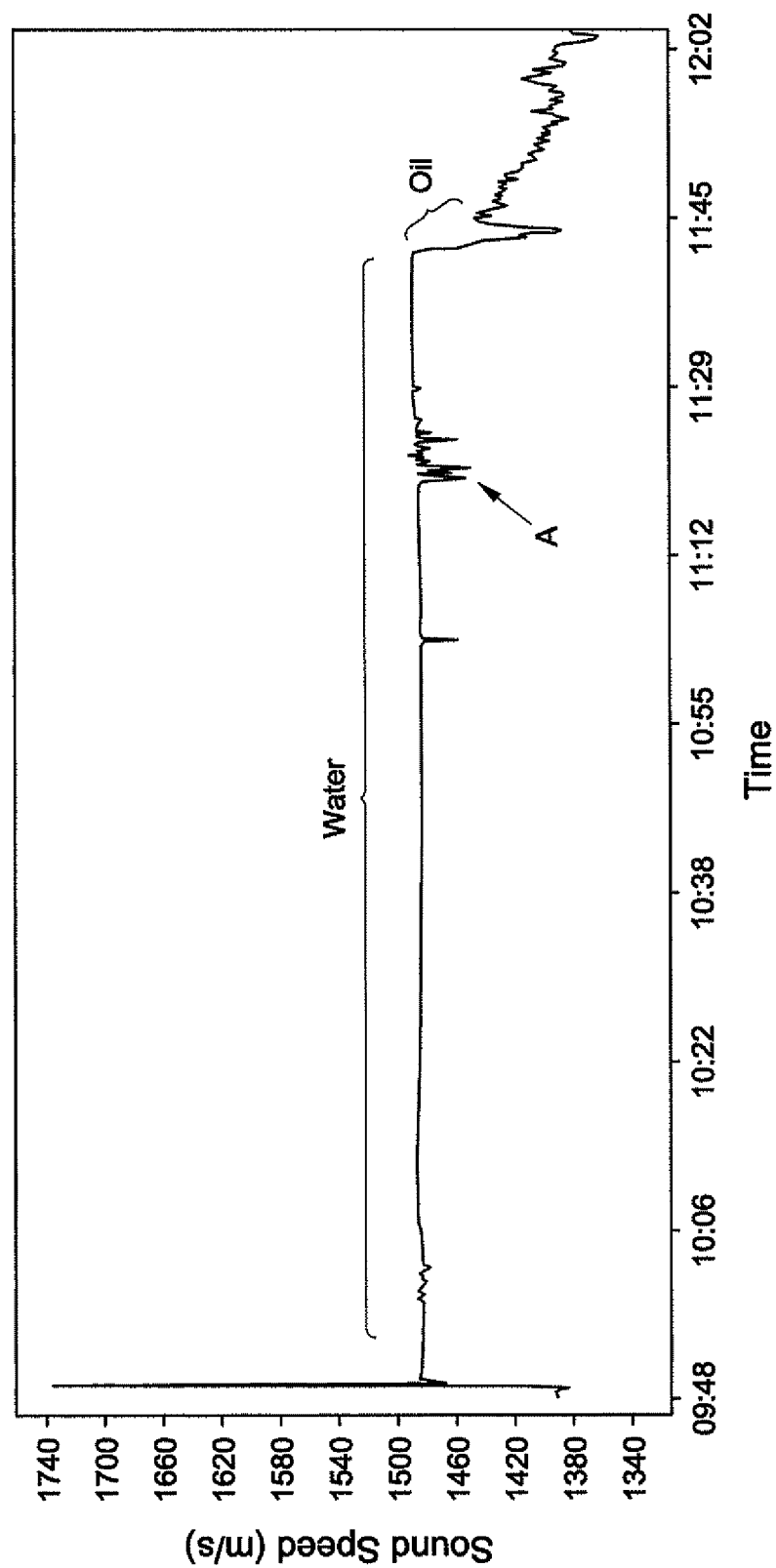

SOUND-VELOCITY DEWATERING SYSTEM

TECHNICAL FIELD OF THE INVENTION

The present invention relates to a method and apparatus for controlling a water stream exiting a dewatering tank, including automatic or remote drainage of water in hydrocarbon tanks.

BACKGROUND OF THE INVENTION

Water level build-up in hydrocarbon storage tanks is an unfortunate and inevitable side effect in oil production. In order to avoid sending this unwanted byproduct to downstream refineries, operators manually discharge the water from the storage tank using drain lines. However, this task requires large amounts of man-power, which prevents the operators from focusing on more important tasks, as well as placing the operators at risk of injury or exposure to chemicals. In addition, failure to adequately drain water from the hydrocarbon tanks can cause processing issues for subsequent refineries.

Automatic tank dewatering apparatuses have been introduced; however, they suffer from serious drawbacks such as: requiring major modifications in the tank or the drain piping for installation, requiring frequent calibration and/or maintenance, running the risk of service buildup on the sensors/transducers, and having high costs to implement. FIG. 1 represents an example of automatic tank dewatering apparatuses of the prior art. Dewatering tank 10 has first probe 12 and second probe 14 that are disposed on the inside of dewatering tank 10 so that probes 12, 14 can sense what type of fluid is at certain depths of dewatering tank 10. First probe 12 monitors water concentrations at or neat the bottom of dewatering tank 10. When concentrations reach a predetermined level, first probe 12 triggers the opening of controllable valve 16 on drain line 18. When water concentrations begin to decrease due to drainage, first probe 12 triggers the closing of controllable valve 16. In the event that first probe 12 fails to trigger the closing of controllable valve 16, second probe 14 will trigger both an alarm (not shown) and the closing of controllable valve 16. However, automatic dewatering tanks in accordance with FIG. 1 suffer from expensive installation and require shutdowns in the event of installation, maintenance, calibration, or failure.

Therefore, it would be beneficial to provide a method and an automatic tank dewatering apparatus that was easy to install, did not require frequent calibration or maintenance, was non-invasive, and had a relatively low cost to implement and operate.

SUMMARY OF THE INVENTION

The present invention is directed to an apparatus and method that satisfies at least one of these needs. In one embodiment, the invention provides for an apparatus for controlling a water stream exiting a dewatering tank, including automatic or remote drainage of water in hydrocarbon tanks. The apparatus can include a sound velocity detector, a control system, and a control element. In another embodiment, the apparatus can optionally include the dewatering tank, the drain line, and a controllable valve. The sound velocity detector can include a transducer, a detector, and a transmitter. In one embodiment, the transducer and the detector can be combined into one piece of equipment, such as a transceiver. The control system can include a computer and a program product. The control element can include a controllable valve. The transducer is operable to emit wave energy through a water stream contained in a drain line of a dewatering tank, and the detector is operable to receive the wave energy from the transducer after the wave energy has passed through the water stream. The transmitter is in electronic communication with the detector and the computer. The transmitter is operable to convert the wave energy received by the detector into a readable signal that is received by a signal processing device defined by the computer. The program product is stored in memory, is in electronic communication with the signal processing device, and is operable on the signal processing device. In one embodiment, the program product is composed of instructions that can convert the readable signal upon receipt into a measured velocity, compare the measured velocity against a predetermined value range, and take a corrective action if the measured velocity is outside the predetermined value range. The control element can be operable to control the flow of the water stream exiting the dewatering tank. In one embodiment, the sound velocity detector can be a non-wetted design (clamp-on). In another embodiment, the sound velocity detector can be a wetted design (inserted or spool-piece).

In one embodiment of the automatic dewatering invention, the step of taking a corrective action can include sending a signal to the controllable valve connected to the drain line to close if the measured velocity is outside the predetermined value range. In another embodiment, the step of taking a corrective action can include sending an alert signal to an operator if the measured velocity is outside the predetermined value range. The apparatus can include an absence of a temperature or a pressure probe.

In another embodiment, the apparatus can include a temperature probe for sensing the temperature of the water stream, wherein the temperature probe is in electronic communication with the transmitter, wherein the transmitter is operable to convert the temperature sensed by the temperature probe into the readable signal, wherein the program product also includes instructions executable for converting the readable signal into a measured temperature. This temperature measurement can be wetted or non-wetted. The temperature measurement can be helpful to provide for more accurate sound-velocity measurements by accounting for velocity variations due to temperature.

In another embodiment, the drain line is in fluid communication with the dewatering tank, and the controllable valve is disposed on the outer surface of the drain line and is in communication with the computer, such that the controllable valve is operable to control the flow of the water stream. Advantageously, in one embodiment of the present invention, the apparatus can be installed onto the drain line while the dewatering tank is in operation. No draining or interruption of operation would be necessary.

Another embodiment of the present invention is drawn to a method for controlling hydrocarbon content in the water stream exiting a dewatering tank system containing the controllable valve having positions. The method can include the steps of emitting wave energy through the water stream contained in the drain line connected to the dewatering tank, receiving the wave energy through the detector, determining the velocity of the wave energy, comparing the velocity of the wave energy to the predetermined value range, and controlling the position of the controllable valve, wherein the controllable valve is in an open position if the velocity of the wave energy is within the predetermined value range and in a closed position if the velocity of the wave energy is outside the predetermined value range.

In another embodiment, the method can also include the steps of converting the wave energy received into the readable signal and transmitting the readable signal to the computer defining the signal processing device having non-transitory computer memory. The signal processing device can have the program product stored in memory that is operable on the signal processing device. The program product is preferably composed of instructions executable for converting the readable signal upon receipt into the measured velocity, comparing the measured velocity against the predetermined value range, and sending the signal to the controllable valve to close if the measured velocity is outside of the predetermined value range. In one embodiment, the method can be conducted in a non-invasive fashion. In another embodiment, the transducer and detector are both disposed outside of the drain line. In another embodiment, the controllable valve is set to the closed position if no wave energy is received by the detector or if there is no measured velocity.

In another embodiment, the method for controlling hydrocarbon content in the water stream exiting the dewatering tank system includes the steps of transmitting sound energy through the water stream flowing in the drain line connected to the dewatering tank in the dewatering tank system, calculating the velocity of the sound energy as the sound energy travels through the water stream, monitoring the velocity of the sound energy for a period of time, and controlling the position of the controllable valve, wherein the controllable valve is biased to the closed position if the velocity of the sound energy changes by more than a predetermined amount within a set time. In one embodiment, the predetermined amount is 70 m/s and the set time is 1 second.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

FIG. 3b is a graphical representation of experimental results recorded in accordance with an embodiment of the present invention.

FIG. 4 is a graphical representation of experimental results recorded in accordance with an embodiment of the present invention.

DETAILED DESCRIPTION

While the invention will be described in connection with several embodiments, it will be understood that it is not intended to limit the invention to those embodiments. On the contrary, it is intended to cover all the alternatives, modifications and equivalence as may be included within the spirit and scope of the invention defined by the appended claims.

One embodiment of the invention provides for an apparatus for controlling hydrocarbon content in the water stream exiting the dewatering the tank. The apparatus can include the sound velocity detector, a control system, and a control element. Preferably, the sound velocity detector includes transducers, an transmitter, and an optional temperature probe. The control system can be a distributed control system (DCS), a terminal monitoring system (TMS), a programmable logic controller (PLC), or any other similar customizable control system. The control system can be either mounted in the field or in a control room. Examples of control elements include an air-operated valve with a solenoid, a motor operated valve (MOV), or the like.

Preferably, the sound velocity detector can provide data to the control system via 4-20 mA, modbus, serial link, foundation fieldbus, radio signals, or other acceptable communication protocol. Types of data that can be measured by the sound velocity detector can include sound velocity, flow measurement, volume measurement, temperature of the liquid, and outside air temperature. In one embodiment, the transducers can measure the sound-velocity of the water stream and communicate it to the transmitter, which in turn can communicate the signal to a display device that can display the measured data. Preferably, the water stream fully encompasses the inner volume of the drain line at the point of measurement. In one embodiment, the transducers can be located on a vertical section of the drain line.

The control system is operable to receive the sound-velocity signal from the sound velocity detector and display the data. The control element is placed in the open position to allow for draining of water within the dewatering tank. Preferably, the control element will be closed automatically once the sound velocity detector identifies non-water media in the water stream. In one embodiment, the control element can be located upstream or downstream the sound velocity detector.

Embodiments of the present invention allow for a simple solution for automating dewatering systems. They can be installed while the dewatering tank is in service and does not require any piping modifications to the drain line. In one embodiment, a commercially available ultrasonic flowmeter can be used as the transducer, detector, and the A/D converter. Advantageously, additional data such as flow and volume measurements can be simultaneously collected, which can be helpful in leak detections in the event of a malfunctioning controllable valve.

Figure 1:
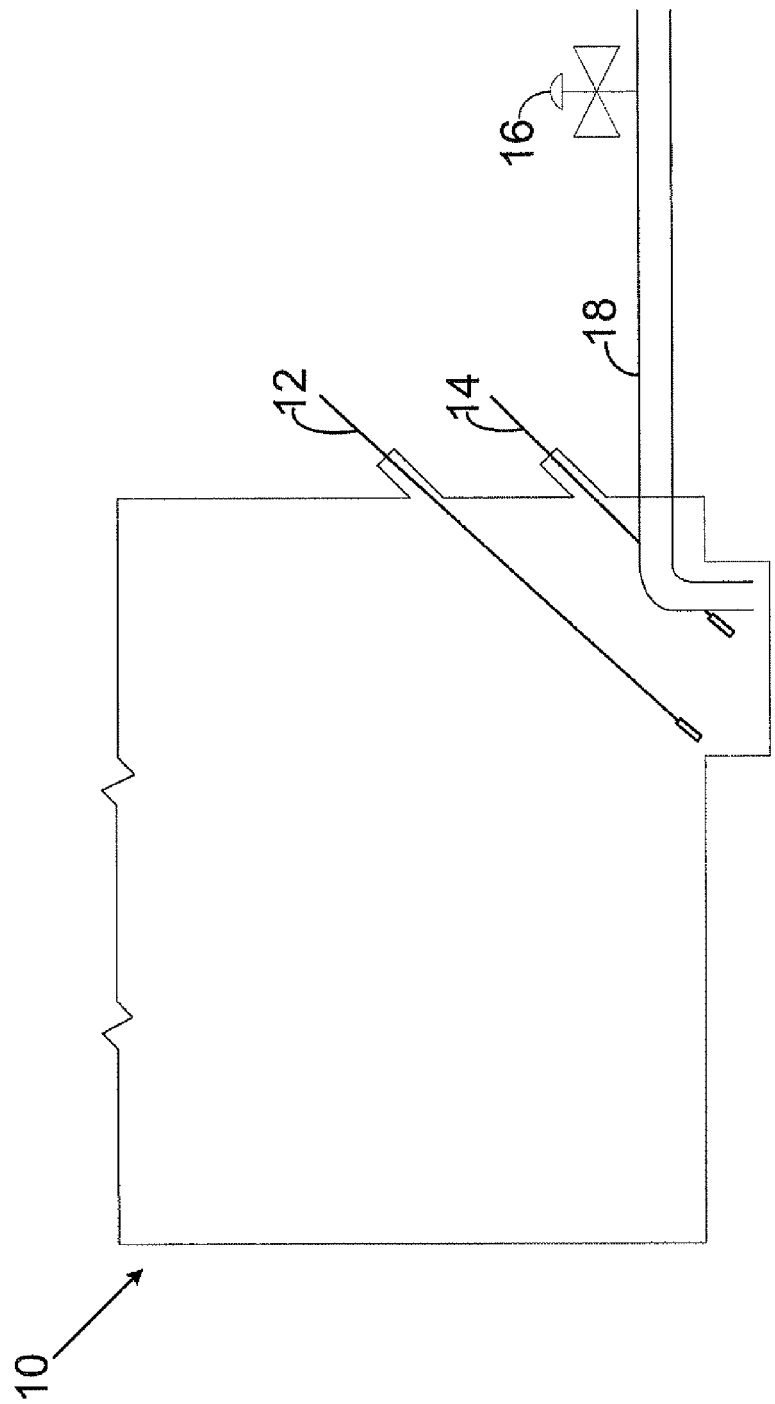
FIG. 1 is a representation of a prior automatic dewatering tank systems.
Figure 2:
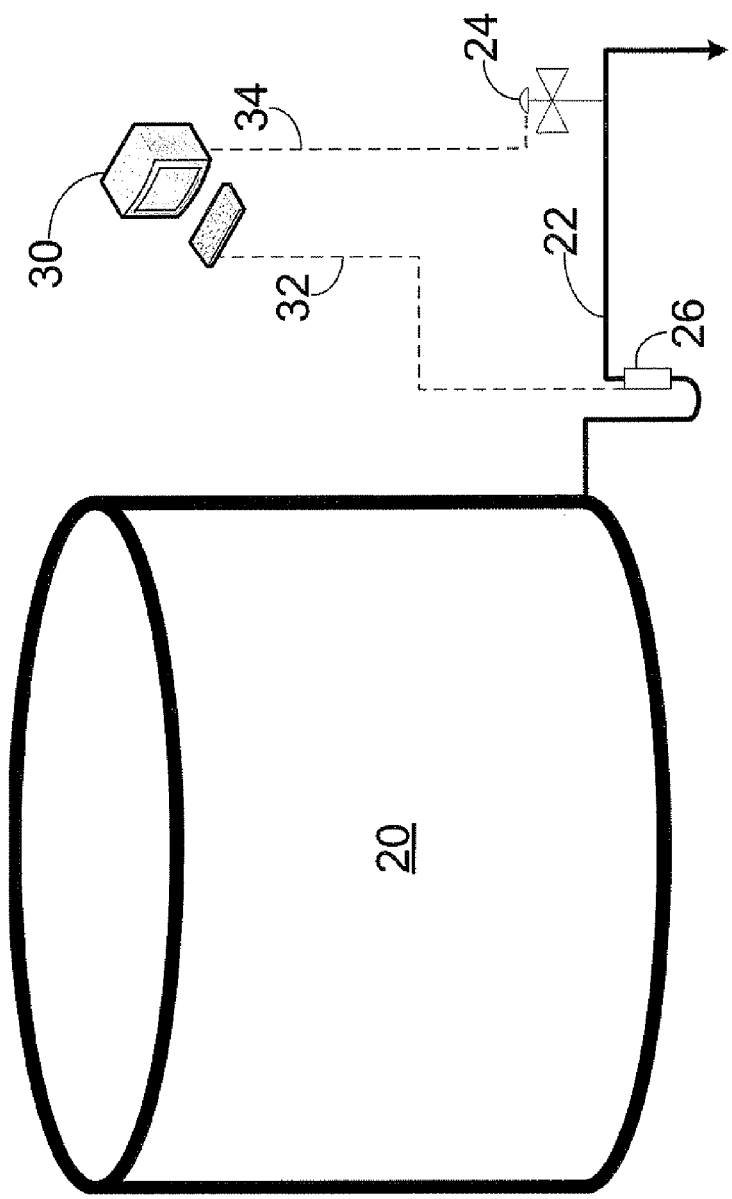
FIG. 2 is a representation of an embodiment of the present invention.

In FIG. 2, dewatering tank 20 contains hydrocarbons and water. Because the hydrocarbons are less dense than the water, the hydrocarbons float to the top, and the water settles to the bottom, thus forming two layers. Drain line 22 is generally disposed on the bottom portion of dewatering tank 20 in order to remove water as opposed to hydrocarbons. Sound velocity detector 26 is preferably disposed on a vertical section of drain line 22 in order to ensure that there is a full volumetric flow at the point where the measurements are being taken; however, those of ordinary skill in the art will recognize that use of the vertical section is not a requirement. Control system 30 is in electronic communication 32 with sound velocity detector 26. Control system includes controllable valve 24, which is in electronic communication 34 with control system 30. Controllable valve 24 is open when only water is detected and is closed when oil is detected.

Experimental Results

A sound velocity detector was used to measure the sound velocity of crude oil, crude-water mixture and water at service temperature. The results are summarized in Table I below:

TABLE I

Velocity Measurements for Fluids

| Fluid Type | Temperature (° C.) | Velocity (m/s) |
|---|---|---|
| Water Sonic Velocity | 44 | 1547 |
| Water/Oil Sonic Velocity | 47 | 1500 |
| Crude Oil | 44 | 1300 |

A Flexim HPI meter was used as the sound velocity detector for these experiments; however, those of ordinary skill in the art will recognize that other sound velocity detectors can be used. The sound velocity detector was installed on drain lines of various crude tanks (tanks 945-V-5, 6, 7). Five tests were conducted to test the concept, the meter reading accuracy, and repeatability.

The general experimental setup and results were as follows: after the drain pipe was in-place and the sound velocity detector was clamped-on, the controllable valve was opened to allow the water to drain. The sound velocity detector started recording velocity measurements. The minute the flow-meter detected a drop in sonic velocity (roughly at least 70 m/s), crude/water mix or crude was observed at the drain. This test was done four more times with identical observations.

Figure 3A:
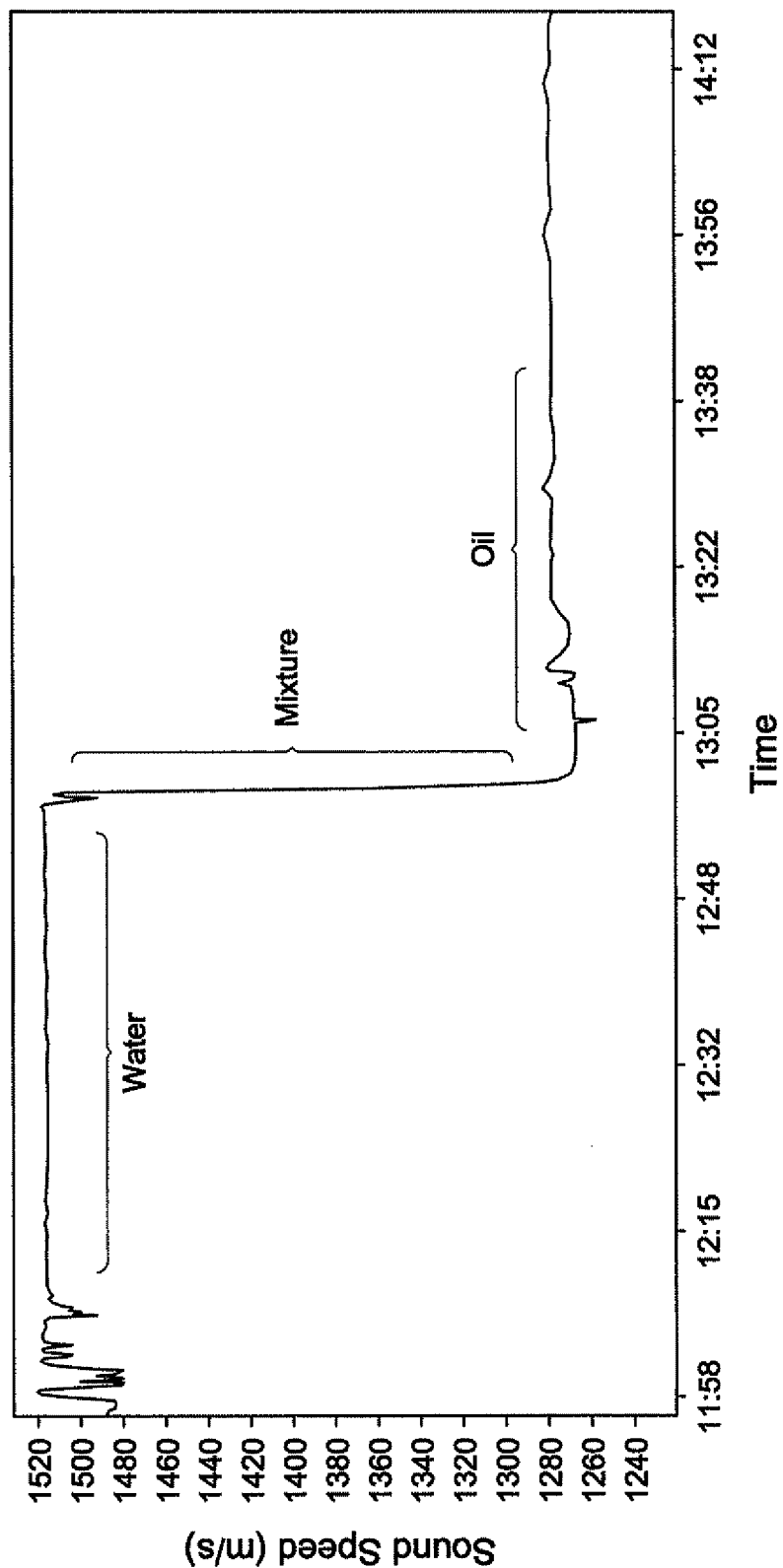
FIG. 3a is a graphical representation of experimental results recorded in accordance with an embodiment of the present invention.

FIG. 3a and FIG. 3b are graphical representations of the results obtained in another experiment. FIG. 3a differs from FIG. 3b only in the scale of time shown on the x-axis. FIG. 3a depicts data for a little more than two hours, whereas FIG. 3b depicts data for approximately seven minutes. The same drain line used in the experiment depicted in FIG. 3 was also used for FIG. 3a and FIG. 3b; however, the Flexim G6725 portable sound velocity detector was used, along with an additional temperature probe. The measurements were recorded every second. The reading for this experiment when water was observed was approximately 1515 m/s and approximately 1275 m/s for when oil was observed.

FIG. 4 is a graphical representation of the results obtained in another experiment. This experiment employed the Flexim F601 portable sound velocity detector in combination with a temperature probe on a drain line of a second dewatering tank. The reading for this experiment when water was observed was approximately 1477 m/s and approximately 1382 m/s for when oil was observed. The small spike occurring at point A was due to a sudden manual valve operation. During this spike, the velocity did not drop below 1443 m/s.

Figure 5:
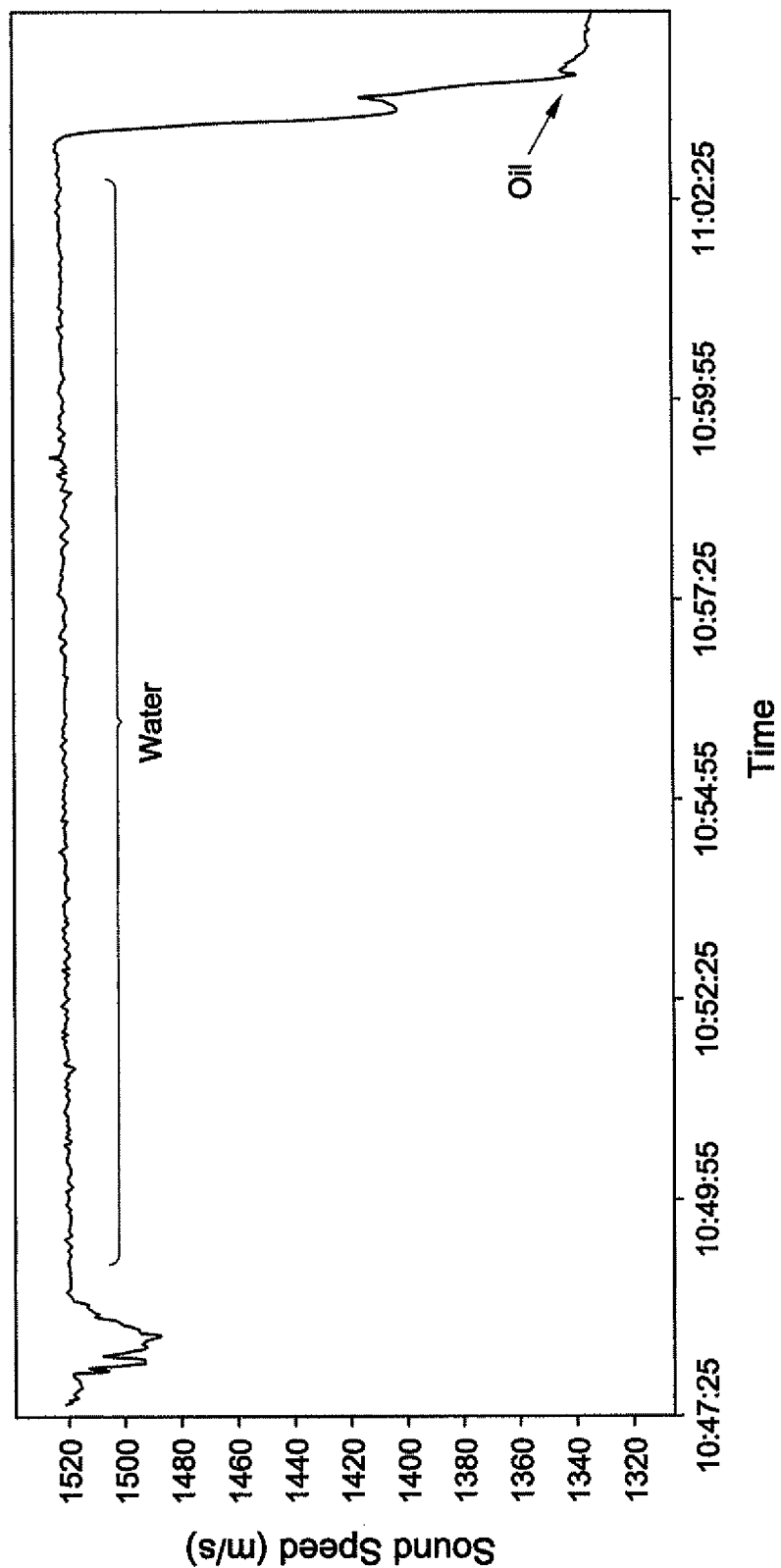
FIG. 5 is a graphical representation of experimental results recorded in accordance with an embodiment of the present invention.

FIG. 5 is a graphical representation of the results obtained in another experiment. This experiment employed the Flexim F601 portable sound velocity detector in combination with a temperature probe on a drain line of a third dewatering tank. The reading for this experiment when water was observed was approximately 1519 m/s and approximately 1330 m/s for when oil was observed. The initial drop in velocity was due to a small quantity of crude that was already in the line when the operator opened the valve. During this portion, the measured velocity did not drop below 1486 m/s.

Figure 6:
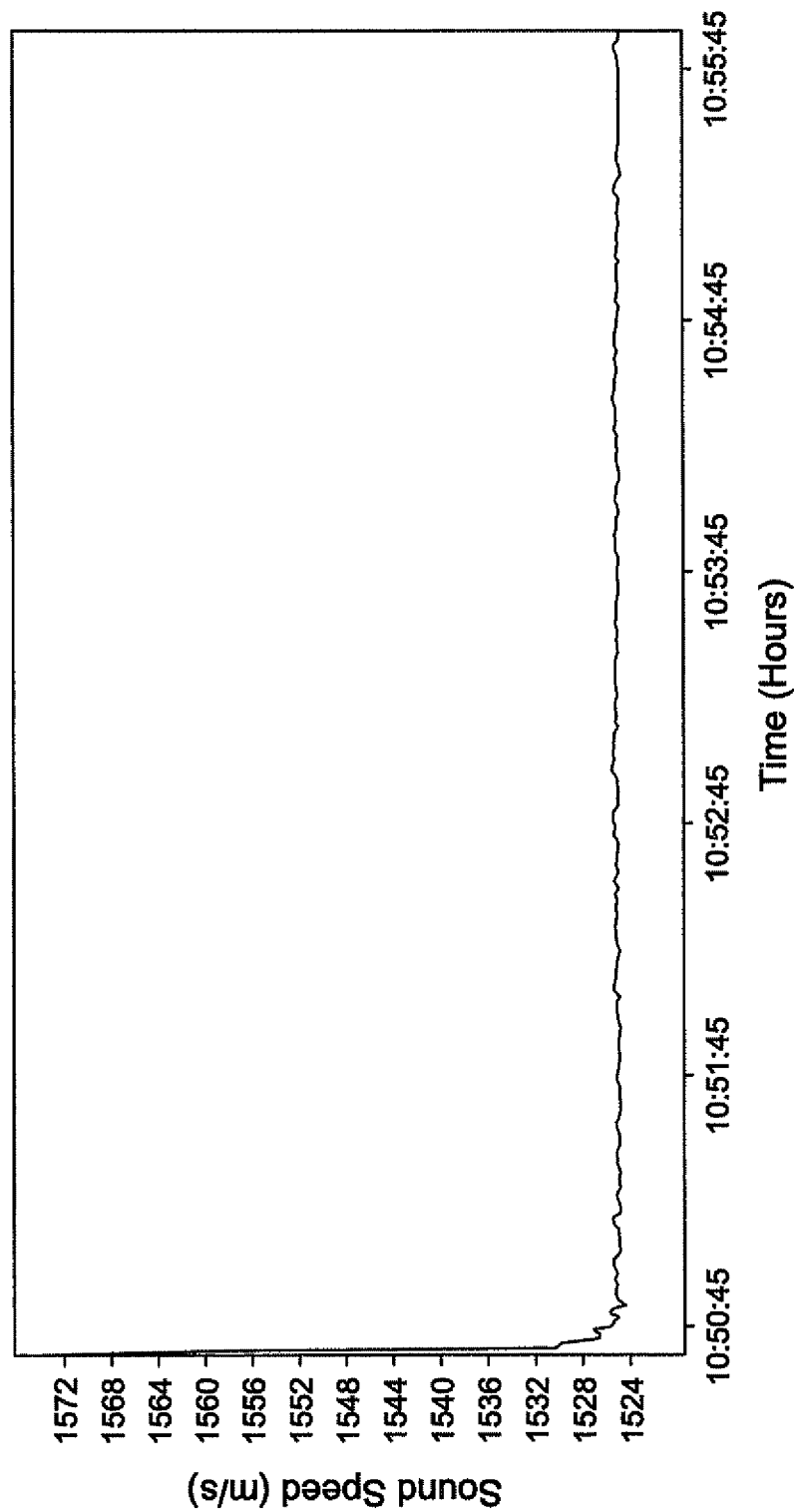
FIG. 6 is a graphical representation of experimental results recorded in accordance with an embodiment of the present invention.

FIG. 6 is a graphical representation of the results obtained in another experiment. This experiment employed the Flexim G6725 portable sound velocity detector on an old pipe that had internal crude build up. Only water was flowed through the pipe to determine how internal crude build up would affect the results. As shown in FIG. 6, the experiment indicates that the sound velocity was approximately 1524 m/s, which indicates that the crude oil build up had little affect on the viability of the invention, even for older pipes having extensive build-up.

Table II below provides a summary of the experimental conditions and results that are shown in FIG. 3-FIG. 6.

TABLE II

Summary of Experimental Conditions and Results

| Figure | Tank | Detector Model | Temperature Probe | Water Velocity (m/s) | Oil Velocity (m/s) |
|---|---|---|---|---|---|
| 3a | 945-V-5 | G6725 | Yes | 1516 | 1275 |
| 3b | 945-V-5 | G6725 | Yes | 1516 | 1275 |
| 4 | 945-V-7 | F601 | Yes | 1477 | 1382 |
| 5 | 945-V-6 | F601 | Yes | 1519 | 1330 |
| 6 | n/a | G6725 | No | 1524 | n/a |

Figure 7:
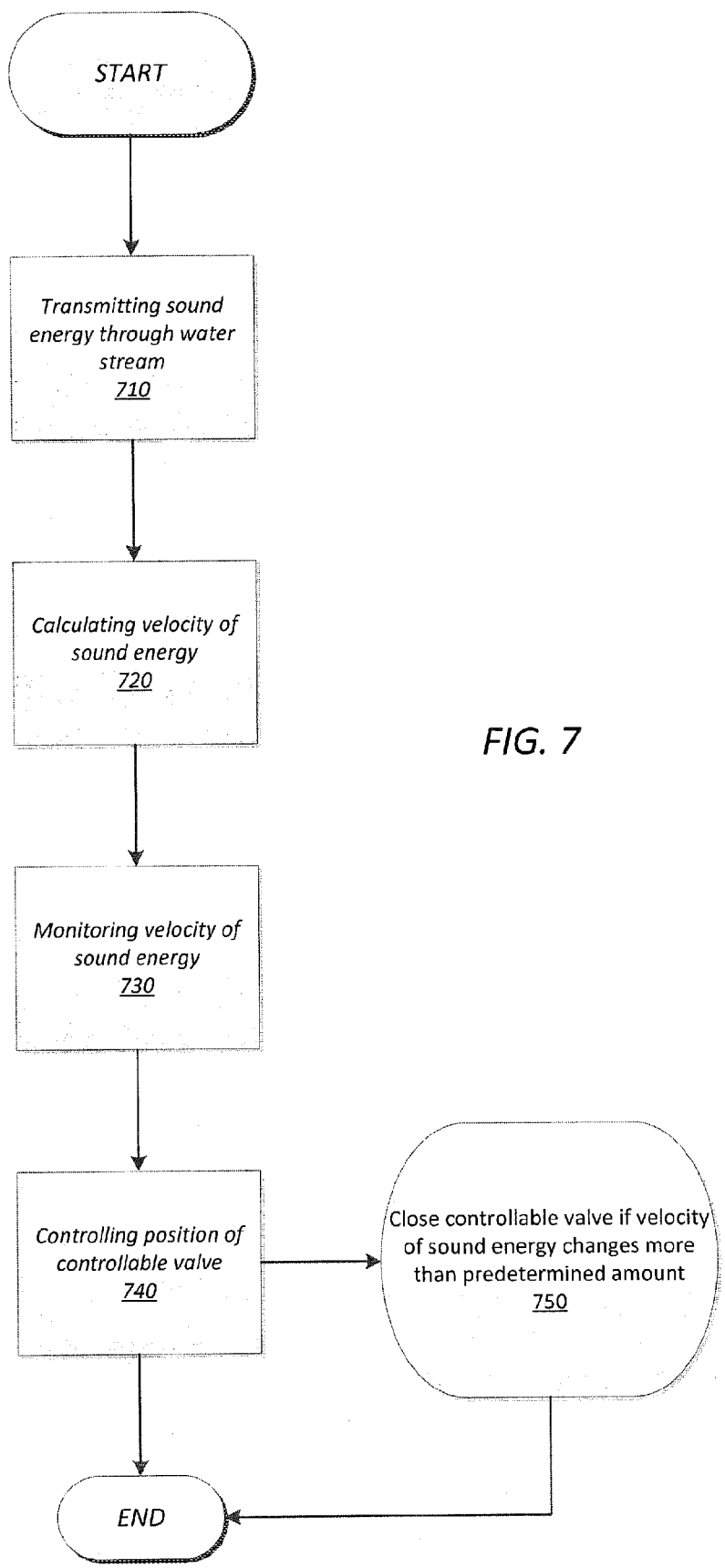
FIG. 7 is a graphical representation of a method for controlling a water stream exiting a dewatering tank system containing a controllable valve in accordance with an embodiment of the present invention.

FIG. 7 is a graphical representation of a method for controlling a water stream exiting a dewatering tank system containing a controllable valve in accordance with an embodiment of the present invention. The method includes transmitting, at step 710, sound energy through a water stream flowing in a drain line connected to a dewatering tank in the dewatering tank system, and calculating, at step 720, a velocity of the sound energy as the sound energy travels through the water stream. The method further includes monitoring, at step 730, the velocity of the sound energy for a period of time, and controlling, at step 740, the position of the controllable valve. According to a step 750 of the method, the controllable valve is biased to a closed position if the velocity of the sound energy changes by more than a predetermined amount within a set time.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed.

We claim:

1. An apparatus for controlling a water stream exiting a dewatering tank, the apparatus comprising:
   a sound velocity detector comprising:
      a transducer operable to emit wave energy through the water stream contained in a drain line of the dewatering tank, the drain line configured to remove only water from the dewatering tank;
      a detector operable to receive the wave energy from the transducer after the wave energy has passed through the water stream; and
      a transmitter in electronic communication with the detector, the transmitter operable to convert the wave energy received by the detector into a readable signal;
   a control system comprising:
      a computer defining a signal processing device having non-transitory computer memory, the computer in electronic communication with the transmitter, the signal processing device operable to receive the readable signal from the transmitter;

a program product stored in memory and operable on the signal processing device, the program product in electronic communication with the signal processing device, the program product composed of instructions executable for:
(1) converting the readable signal upon receipt into a measured velocity,
(2) comparing the measured velocity against a predetermined value range, and
(3) taking a corrective action if the measured velocity is outside the predetermined value range, indicating a presence of hydrocarbons in the water stream; and
a one-way control element configured to move to a closed position to stop the flow of the water stream exiting the dewatering tank, when the corrective action is taken.

2. The apparatus of claim 1, wherein the control element comprises a controllable valve that is connected to the drain line, wherein the step of taking a corrective action comprises sending a signal to the controllable valve to close if the measured velocity is outside the predetermined value range.

3. The apparatus of claim 1, wherein the step of taking a corrective action comprises sending an alert signal to an operator if the measured velocity is outside the predetermined value range.

4. The apparatus of claim 1, further comprising an absence of a temperature probe.

5. The apparatus of claim 1, further comprising an absence of a pressure probe.

6. The apparatus of claim 1, further comprising a temperature probe for sensing the temperature of the water stream, wherein the temperature probe is in electronic communication with the transmitter, wherein the transmitter is operable to convert the temperature sensed by the temperature probe into the readable signal, wherein the program product also includes instructions executable for converting the readable signal into a measured temperature.

7. The apparatus of claim 1, further comprising the dewatering tank, the dewatering tank containing liquid hydrocarbons and water.

8. The apparatus of claim 7, further comprising:
the drain line, the drain line in fluid communication with the dewatering tank; and
a controllable valve disposed on an outer surface of the drain line and in communication with the computer, the control valve operable to control the flow of the water stream.

9. The apparatus of claim 8, wherein the transducer and the detector are disposed on a vertical section of the drain line.

10. A method for controlling a water stream exiting a dewatering tank system containing a one-way controllable valve, the method comprising the steps of:
(a) emitting wave energy through a water stream contained in a drain line connected to a dewatering tank in the dewatering tank system, the wave energy emitted using a transducer, and the drain line configured to remove only water from the dewatering tank;
(b) receiving the wave energy through a detector;
(c) determining the velocity of the wave energy;
(d) comparing the velocity of the wave energy to a predetermined value range; and
(e) controlling a position of the one-way controllable valve, wherein the one way controllable valve is in an open position if the velocity of the wave energy is within the predetermined value range and in a closed position if the velocity of the wave energy is outside the predetermined value range, indicating a presence of hydrocarbons in the water stream.

11. The method of claim 10, wherein steps (c) thru (e) are further comprised of the steps of:
converting the energy value received in step (b) into a readable signal; and
transmitting the readable signal to a computer defining a signal processing device having non-transitory computer memory, the signal processing device having a program product stored in memory and operable on the signal processing device, the program product composed of instructions executable for:
(1) converting the readable signal upon receipt into a measured velocity,
(2) comparing the measured velocity against the predetermined value range, and
(3) sending a signal to the controllable valve to close if the measured velocity is outside of the predetermined value range.

12. The method of claim 10, wherein the method is conducted in a non-invasive fashion.

13. The method of claim 10, wherein the transducer and the detector are both disposed outside of the drain line.

14. The method of claim 10, wherein the controllable valve is set to the closed position if there is no measured velocity.

15. The method of claim 10, wherein the predetermined value range is from 1475 to 1575 m/s.

16. The method of claim 10, wherein the wave energy is sound waves.

17. A method for controlling a water stream exiting a dewatering tank system containing a one-way controllable valve, the method comprising the steps of:
(a) transmitting sound energy through a water stream flowing in a drain line connected to a dewatering tank in the dewatering tank system, the drain line configured to remove only water from the dewatering tank;
(b) calculating a velocity of the sound energy as the sound energy travels through the water stream;
(c) monitoring the velocity of the sound energy for a period of time; and
(d) controlling a position of the one-way controllable valve, wherein the one-way controllable valve is closed if the velocity of the sound energy changes by more than a predetermined amount within a set time, indicating a presence of hydrocarbons in the water stream.

18. The method of claim 17, wherein the predetermined amount is 70 m/s and the set time is 1 second.

* * * * *